United States Patent [19]

Omura et al.

[11] Patent Number: 5,064,495
[45] Date of Patent: Nov. 12, 1991

[54] METHOD OF ADHESION WITH A MERCAPTO GROUP CONTAINING ADHESIVE

[75] Inventors: Ikuo Omura; Junichi Yamauchi; Mitsunobu Kawashima, all of Kurashiki, Japan

[73] Assignee: Kuraray Company, Limited, Kurashiki, Japan

[21] Appl. No.: 379,666

[22] Filed: Jul. 13, 1989

Related U.S. Application Data

[63] Continuation of Ser. No. 103,685, Oct. 2, 1987, abandoned.

[30] Foreign Application Priority Data

Oct. 6, 1986 [JP]  Japan ................................. 61-238946

[51] Int. Cl.$^5$ ..................... C09J 5/00; C09J 141/00
[52] U.S. Cl. ................... 156/307.3; 156/314; 156/326; 156/330.9; 433/217.1; 526/286; 526/288; 526/289

[58] Field of Search ..................... 156/307.3, 314, 315, 156/326, 327, 330.9; 433/217.1, 218.1

[56] References Cited

U.S. PATENT DOCUMENTS

| 3,265,673 | 8/1966 | Richards | 526/286 |
| 3,900,451 | 8/1975 | Mitchell | 526/286 |
| 4,812,363 | 3/1989 | Bell | 428/420 |

FOREIGN PATENT DOCUMENTS

6515280  5/1967  Netherlands .

*Primary Examiner*—Christopher Henderson
*Attorney, Agent, or Firm*—Oblon, Spivak, McClelland, Maier & Neustadt

[57] ABSTRACT

There is provided an adhesive comprising (a) a compound having at least one mercapto group or polysulfide group joined to a saturated carbon atom and at least one olefinic double bond and (b) a solvent which does not copolymerize with said compound or a liquid polymerizable monomer which copolymerizes with said compound.

8 Claims, No Drawings

METHOD OF ADHESION WITH A MERCAPTO GROUP CONTAINING ADHESIVE

This application is a continuation of application Ser. No. 07/103,685, filed on Oct. 2, 1987, now abandoned.

BACKGROUND OF THE INVENTION

1. Field of the Invention

The present invention relates to an adhesive which exhibits good adhesion properties when applied to metals, especially precious metals. The term "adhesive" used in the present invention comprehends primers which are used when a metallic material is bonded to other materials. The adhesive of the present invention is useful particularly in the field of dentistry.

2. Description of the Prior Art

The adhesive of polymerization-curing type composed of polymerizable monomers such as acrylic monomers and epoxy compounds is in general use for the bonding of metallic materials because of its good workability and its ability to cure in a short time at normal temperature under normal pressure. It plays an important role in the field of adhesive. However, it suffers from a serious disadvantage in some application areas where water resistance is required, because it rapidly decreases in bond strength when its bonding interface is exposed to water at all times.

In the field of dental materials, attempts have recently been made to obtain an adhesive of polymerization-curing type which has a high bond strength for metals and good water resistance. These attempts are bearing fruit. An example is the dental adhesive incorporated with an organophosphate ester (as disclosed in U.S. Pat. No. 4,539,382). It produces a high bond strength which is very little affected by water when applied to base metals such as iron, nickel, chromium, cobalt, tin, aluminum, copper, and titanium, and alloys thereof. It is now in practical use as a dental adhesive. Unfortunately, when it is used for dental casting (e.g., inlay, crown, and bridge) of precious metal alloys (e.g., gold, platinum, palladium, and silver alloys), the bond strength is a little more affected by water than when it is used for base metal alloys. To keep the bond strength unaffected by water, it was necessary that the adherend of precious metal alloys undergo surface treatment such as tin plating and oxidation.

It has recently been found that the bond strength for precious metals becomes moderately unaffected by water when an MMA-tributyl borane adhesive is applied to a precious metal adherend primed with N-(4-mercaptophenyl)methacrylamide. This was reported in The Journal of the Japanese Society for Dental Materials and Devices, vol. 5, p. 92–105 (1986).

SUMMARY OF THE INVENTION

As mentioned above, the adhesive disclosed in U.S. Pat. No. 4,539,382 has a disadvantage that the adherend needs surface treatment such as tin plating when it is used to bond a dental material of precious metal or precious metal alloy to a tooth. By contrast, the adhesive containing the above-mentioned N-(4-mercaptophenyl)methacrylamide does not need such a complex procedure. However, it is not practically satisfactory in that the bond strength is affected by water.

It is an object of the present invention to provide a primer (called "adhesive" in the present invention) to treat the adherend surface prior to bonding to ensure firm bonding between a metal (especially precious metal) object and a metal object or a non-metal object. It is also an object of the present invention to provide an adhesive to bond a metal (especially precious metal) object to a metal object or non-metal object.

These objects are achieved by the adhesives (1) and (2) mentioned below.

(1) An adhesive comprising (a) a compound having at least one mercapto group or polysulfide group joined to a saturated carbon atom and at least one olefinic double bond and (b) a solvent which does not copolymerize with said compound.

(2) An adhesive comprising (a) a compound having at least one mercapto group or polysulfide group joined to a saturated carbon atom and at least one olefinic double bond and (b) a liquid polymerizable monomer which copolymerizes with said compound.

DETAILED DESCRIPTION OF THE INVENTION

The present invention is characterized by that the adhesive component is the compound (a) which has at least one mercapto group or polysulfide group joined to a saturated carbon atom and at least one olefinic double bond. Examples of the compound are given below.

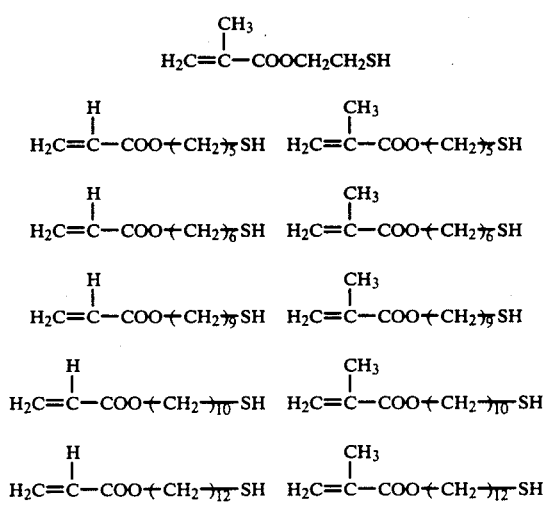

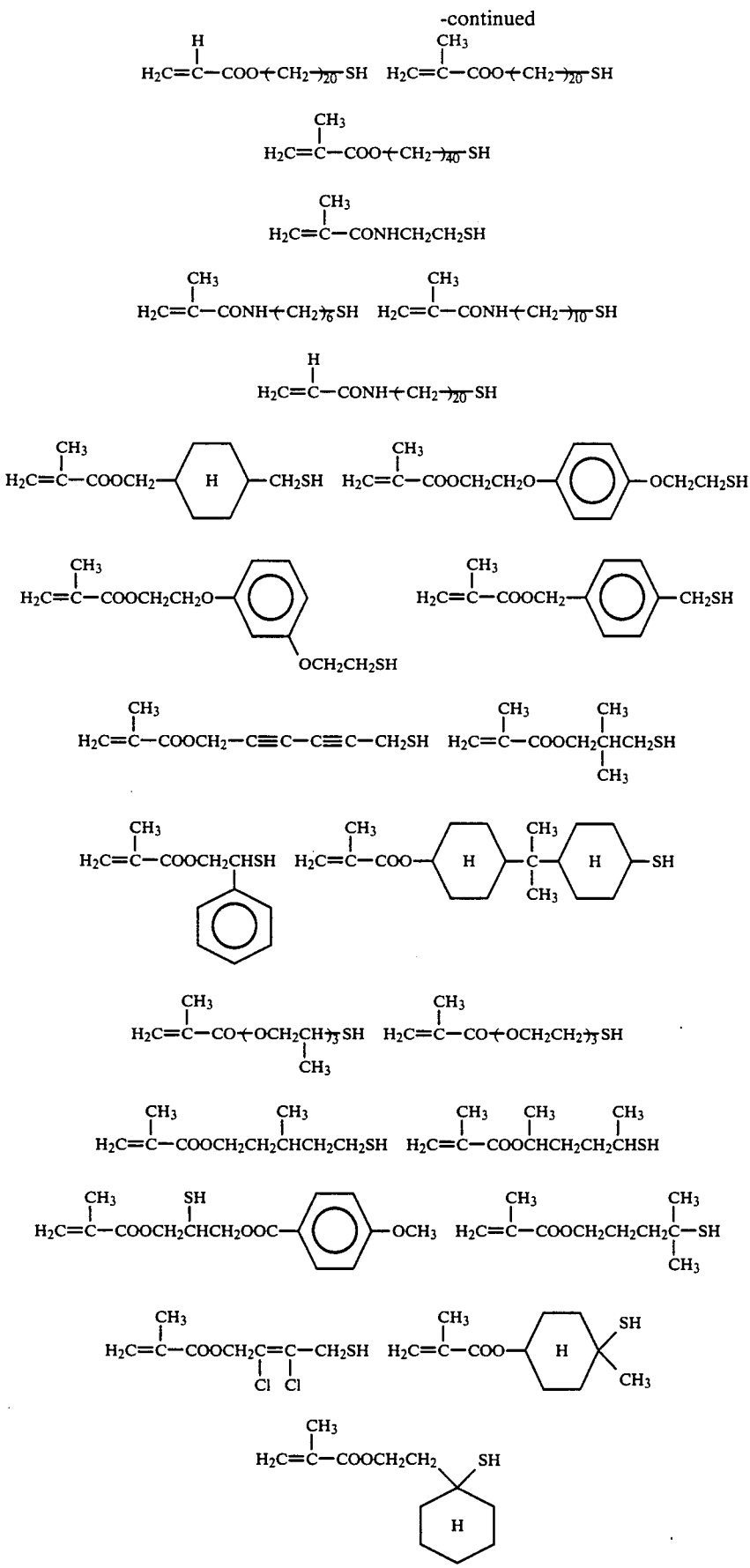

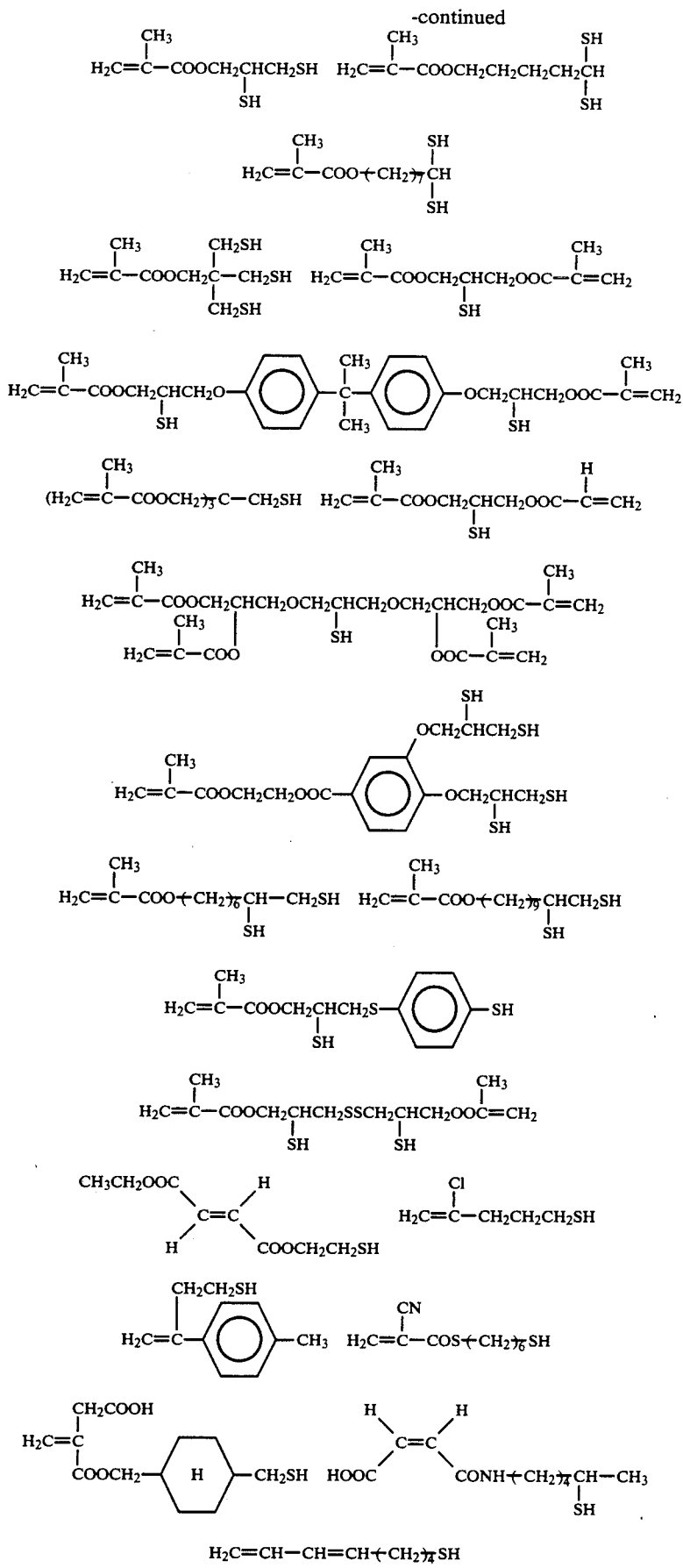

-continued
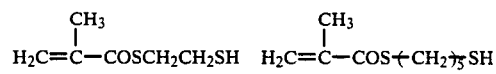
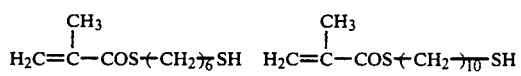
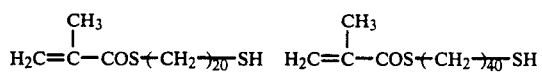
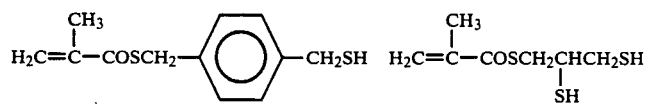
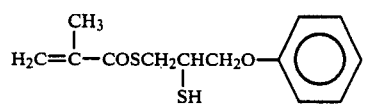
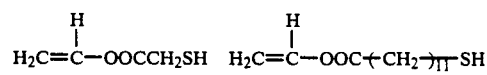
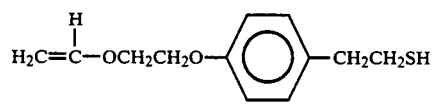
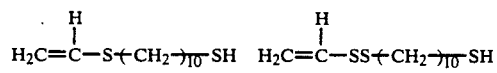
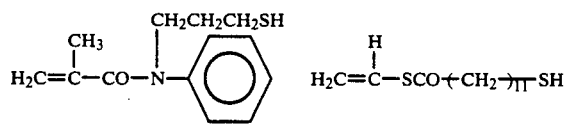
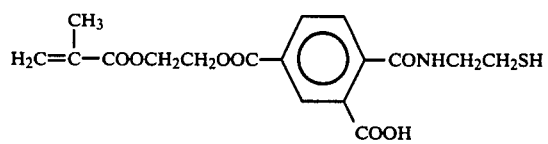
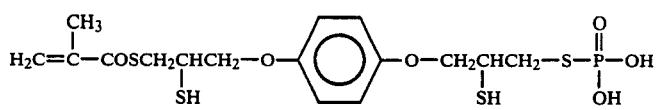
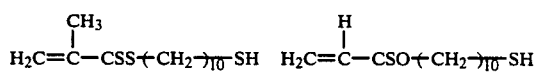
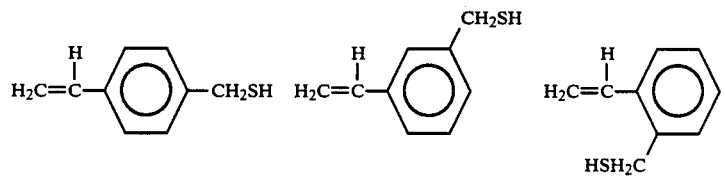
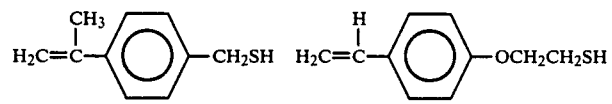

-continued
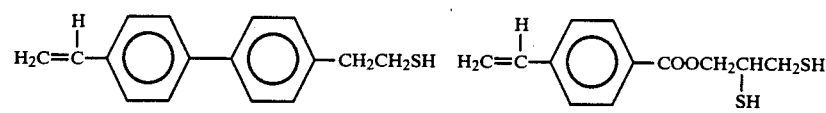
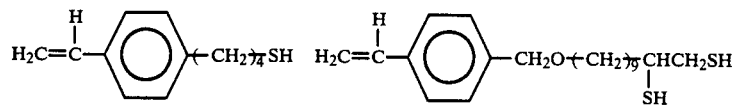
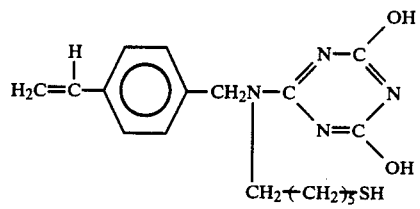
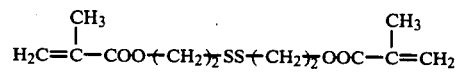
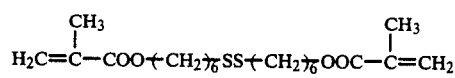
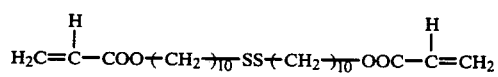
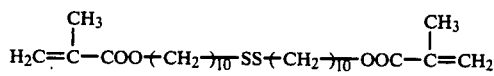
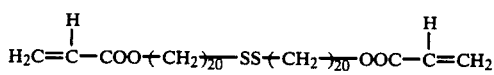
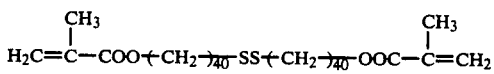
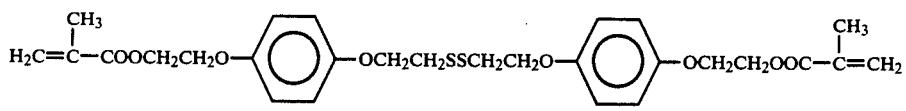
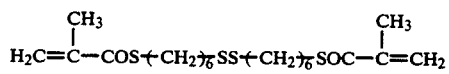
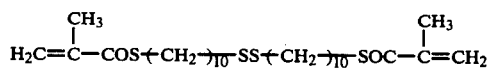
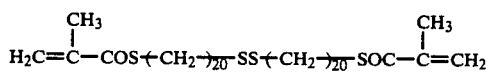
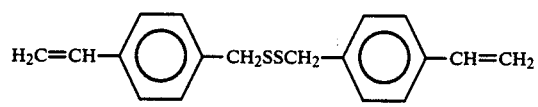

-continued
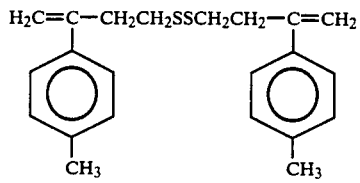
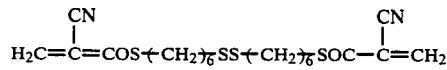
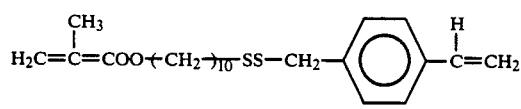
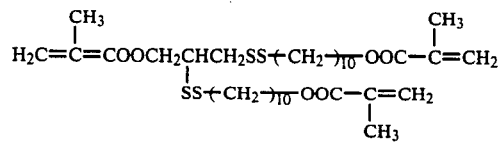
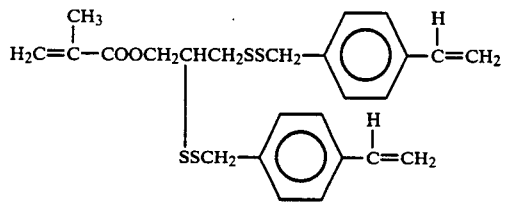
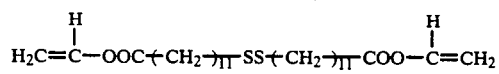
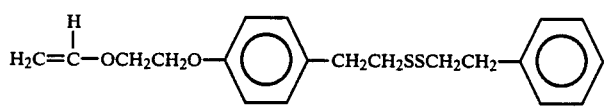
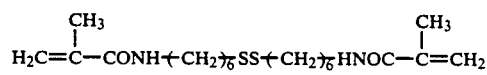
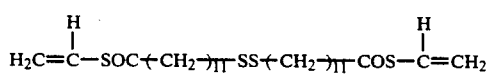
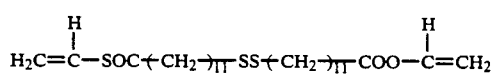

-continued
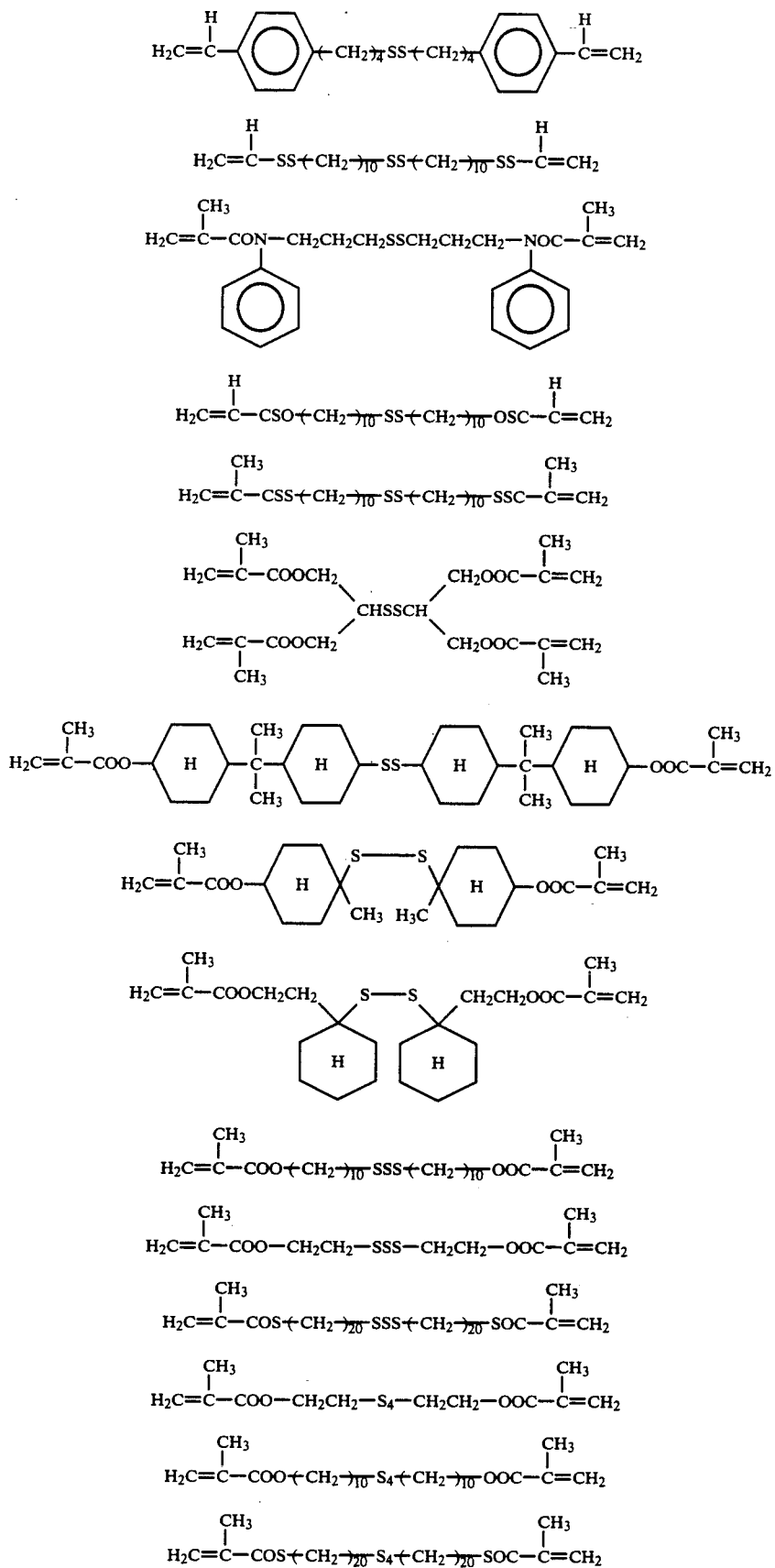

-continued

Among the above-mentioned examples, the thiol compound represented by the formula [I] below or the polysulfide compound represented by the formula [II] below is preferable.

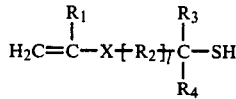  [I]

where $R_1$ denotes a hydrogen atom or methyl group; $R_2$ denotes a $C_1$-$C_{40}$ organic group (which may contain a

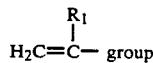

and/or mercapto group); $R_3$ and $R_4$ each denote a $C_1$-$C_{40}$ organic groups (which may contain a

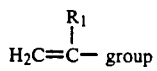

and/or mercapto group), hydrogen atom, mercapto group, or halogen atom; at least two of $R_2$, $R_3$, and $R_4$ may join to each other to form a cyclic structure when $R_3$ and/or $R_4$ is an organic group; X denotes

—COO—, —OOC—, —CONH—, —COS—, —SOC—,

—S—, or 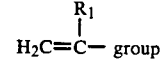;

and l denotes an integer of 0 or 1.

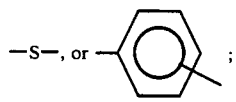  [II]

where $R_1$, l, and X are as defined above; $R_2'$ denotes a $C_1$-$C_{40}$ organic group (which may contain

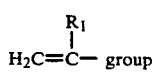

and/or polysulfide group); $R_3'$ and $R_4'$ each denote a $C_1$-$C_{40}$ organic group (which may contain

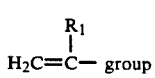

and/or polysulfide group), hydrogen atom, mercapto group, or halogen atom; at least two of $R_2'$, $R_3'$, and $R_4'$ may join to each other to form a cyclic structure when $R_3'$ and/or $R_4'$ is an organic group; $R_5$, $R_6$, and $R_7$ each denote a $C_1$-$C_{40}$ organic group (which may contain

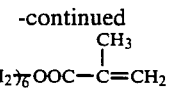

and/or polysulfide group), hydrogen atom, mercapto group, or halogen atom, at least two of $R_5$, $R_6$, and $R_7$ may join to each other to form a cyclic structure when they are organic groups; and l denotes an integer of 2 to 6.

Among the compounds represented by the formulas [I] and [II] above, the compounds represented by the formulas [III] and [IV] are especially practical.

  [III]

where $R_1$ is as defined above; and m denotes an integer of 6 to 20.

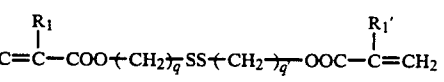  [IV]

where $R_1$ is as defined above; $R_1'$ is the same as $R_1$; and q and q' each denote an integer of 2 to 20.

The above-mentioned compound (a) used as an adhesive component in the present invention can be synthesized according to the process described in "Shin-Jikken Kagaku Koza", Vol. 14, (published by Maruzen, 1977-8), The Chemistry of the Thiol Group (published by John Wiley & Sons, 1974), and Comprehensive Organic Chemistry, Vol. 3 (published by Pergamon Press, 1979).

For example, the compound represented by the formula [I] can be synthesized through any of the following three routes.

(1) Synthesis starts from a compound of the same chemical structure as represented by the formula [I] which has a hydroxyl group, amino group, or halogen atom in place of the mercapto group. The compound of the formula [I] is obtained by replacing the hydroxyl group, amino group, or halogen atom by a mercapto group.

(2) By the condensation of (meth)acrylic acid chloride or (meth)acrylic acid anhydride with a compound represented by the formula [V] below.

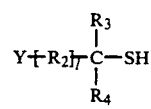  [V]

where $R_2$, $R_3$, $R_4$, and l are as defined in the formula [I]; and Y denotes a mercapto group, hydroxyl group, or amino group.

(3) By the reductive cleavage of the disulfide linkage in a compound represented by the formula [II] in which n is 2.

Incidentally, when the process (1) is applied in the usual way to a compound having an olefinic double bond with a substituent electron attracting group, it is difficult to obtain a compound represented by the formula [I] because the mercaptide ion represented by the formula [VI] below, which occurs as an intermediate, extremely readily attaches to the double bond.

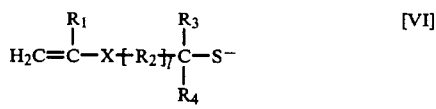

This difficulty can be effectively avoided by adding a large excess of heavy metal ions (such as $Zn^{2+}$, $Pb^{2+}$, $Ag^+$, and $Hg^{2+}$) to the reaction system so that the mercaptide ion [VI] formed is removed and recovered in the form of insoluble metal salt from the reaction system and subsequently treating the metal salt with a strong acid such as hydrochloric acid to liberate the compound of the formula [I].

The compound represented by the formula [II] can be synthesized through either of the following two routes.

(1) By preparing a thiol compound [I] having an olefinic double bond and subsequently changing this compound into a polysulfide by condensation.

(2) By introducing an olefinic double bond into a compound having the polysulfide linkage.

The adhesive of the present invention is prepared from the above-mentioned compound (a) by the following process (1) or (2).

(1) The compound (a) is dissolved in a solvent to give the adhesive. The solvent is a volatile organic solvent having a boiling point lower than 250° C. (e.g., methanol, ethanol, 2-ethyl butanol, acetone, methyl ethyl ketone, diethyl ketone, ethyl ether, n-butyl ether, 1,4-dioxane, tetrahydrofuran, ethyl acetate, toluene, xylene, hexane, octane, methylene chloride, 1,2-dichloroethane, and 1,1,2,2-tetrachloroethane), or water, or a mixture thereof. The concentration of the above-mentioned compound is 0.0001 to 99 wt % (preferably 0.001 to 50 wt %) based on the total amount of the compound and the solvent. To the solution is added a polymerization initiator and copolymerizable monomer (mentioned later), according to need.

The thus obtained adhesive is applied as a primer to the surface of a metal adherend, and subsequently an adhesive or a composite resin used in the usual way is applied to the primer coat to bond the metal adherend to another metal adherend or non-metal adherend.

(2) The compound (a) is dissolved in a monomer which copolymerizes with it to give the adhesive. The copolymerizable monomer is explained later. The concentration of the compound (a) is 0.005 to 99 wt % based on the total amount of the compound and the copolymerizable monomer. To the solution is added a filler and polymerization initiator, according to need. The adhesive of the present invention can also be obtained by adding the compound (a) to a commonly used adhesive (which is composed of a polymerizable monomer and a polymerization initiator and which may contain a filler). In this case, the concentration of the compound (a) should be 0.005 to 99 wt % (based on the total amount of the compound (a) and the copolymerizable monomer).

In the case of (1) above, the compound (a) exhibits the adhesion promoting effect even when its amount is very small, because the effect is attributable to the monomolecular layer formed on the adherend surface by adsorption. This adhesion promoting effect remains even when the primer coat is washed with a solvent.

The adhesive of the present invention is used preferably as a primer. To the primer coat is applied a known adhesive of polymerization curing type, preferably an adhesive containing an acrylic monomer, as mentioned above. The tensile bond strength thus achieved is usually higher than 200 kg/cm², depending on the mechanical strength of the adhesive per se. Almost all failure is cohesive failure or adherend failure. The bond interface has such an extremely good water resistance that the bond strength does not decrease appreciably when the adherend is dipped in water at normal temperature for several months.

The copolymerizable monomer used for the adhesive (especially that mentioned in (2) above) of the present invention should preferably be a (meth)acrylic ester such as methyl methacrylate, 2-hydroxyethyl methacrylate, ethylene glycol dimethacrylate, triethylene glycol dimethacrylate, neopentyl glycol dimethacrylate, 2,2-bis[4-(3-methacryloyloxy-2-hydroxypropoxy)-phenyl]propane (called Bis-GMA), 2,2-bis[methacryloyloxyethoxyphenyl]propane, trimethylolethane triacrylate, pentaerythritol tetraacrylate, 4-(2-methacryloyloxyethyl) trimellitate, 4-methacryloxyethyl trimellitate anhydride, bis(2-methacryloyloxyethyl) hydrogen phosphate, 2-methacryloyloxyethylphenyl hydrogen phosphate, 6-methacryloyloxyhexyl dihydrogen phosphate, 10-methacryloyloxydecyl dihydrogen phosphate, tris(2-methacryloyloxyethyl) phosphate, and N,N-dimethylaminoethyl methacrylate.

The adhesive of the present invention is usually incorporated with a polymerization initiator as mentioned above. It includes benzoyl peroxide-aromatic tertiary amine, peroxide (cumene hydroperoxide, etc.), tributyl borane, and aromatic sulfinic acid (or salt thereof)-aromatic secondary or tertiary amine-acyl peroxide. It further includes photopolymerization initiators such as camphorquinone, camphorquinone-tertiary amine, camphorquinone-aldehyde, and camphorquinone-mercaptan.

In the case where the adhesive of the present invention is used as a primer and another adhesive is applied onto the primer coat, it is not necessary that the adhesive of the present invention contains a polymerization initiator. In such a case, a polymerization initiator in the adhesive migrates into the primer coat to effect polymerization curing of the primer.

The adhesive of the present invention may be incorporated with an inorganic filler such as quartz, glass, hydroxyapatite, calcium carbonate, barium sulfate, titanium oxide, and zirconium oxide; and polymer powder such as poly(methyl methacrylate), polystyrene, and polyvinyl chloride.

The adhesive of the present invention may be applied to precious metals such as gold, platinum, palladium, silver, ruthenium, rhodium, osmium, and iridium; and base metals such as iron, nickel, cobalt, copper, zinc, tin, aluminum, titanium, vanadium, chromium, manganese, zirconium, molybdenum, cadmium, indium, and antimony. It also exhibits the adhesion promoting effect when applied to metal oxides such as aluminum oxide, titanium oxide, and zirconium oxide, and ceramics containing such metal oxides.

Since the adhesive of the present invention provides a high bond strength which is very little affected by water when applied to precious metals, it can be suitably used in the field of dentistry. For example, it is used to bond a precious metal casting such as inlay, crown, and bridge to a tooth. It is also used to prepare a prosthetic appliance of precious metal by bonding a pontic to a bridge frame-work or bonding separately cast parts together. The bonding will provides improved performance and workability which were not achieved with the conventional technique. The adhesive of the present invention can be used not only in the field of dentistry but also in any industrial field where the bonding of metals and metal oxides is necessary.

The invention will be understood more readily by reference to the following examples; however, these examples are intended to illustrate the invention and are not to be construed to limit the scope of the invention.

(Production of thiol compound)

Production Example 1

In a 500-cc three-necked flask was placed 50 g of a mixture composed of 10-hydroxydecyl methacrylate (59%) and 1,10-dimethacryloyloxy decane (41%), and the flask was cooled in an ice bath. 30 g of p-toluene-sulfonyl chloride dissolved in 60 cc of pyridine was slowly added dropwise with stirring through a dropping funnel connected to the flask. The reaction temperature was kept at 0° C. for 2 hours, and then raised to room temperature. Stirring was continued for 2 hours, and the reaction product was neutralized with 6N HCl. The liberated organic substance was extracted with methylene chloride, followed by washing with water several times and drying with anhydrous magnesium sulfate. After the addition of 0.1 g of hydroquinone monomethyl ether, the methylene chloride was evaporated away at a temperature below 40° C. under reduced pressure. Thus there was obtained 79 g of a mixture composed of p-toluenesulfonate of 10-hydroxydecyl methacrylate and 1,10-dimethacryloyloxy decane.

This mixture together with 11 g of thiourea and 0.4 g of 2,2'-methylenebis(4-ethyl-6-tert-butylphenol) were dissolved in 150 cc of ethanol. The solution was refluxed for 30 minutes and then ethanol was evaporated away under reduced pressure. The residues were extracted with acetonitrile and acetonitrile was evaporated away under reduced pressure from the extract. Thus there was obtained a crude isothiuronium salt. It was washed with a large amount of n-hexane to remove 1,10-dimethacryloyloxy decane. Thus there was obtained a isothiuronium salt of high purity.

In methanol were dissolved 48 g of the isothiuronium salt and 40 g of zinc chloride. With vigorous agitation, a methanol solution of sodium hydroxide was added dropwise to form a white precipitate of zinc salt of 10-mercaptodecyl methacrylate. The addition was continued until no precipitate appeared any longer. The salt was filtered out and washed with water, followed by drying. The amount of the salt obtained was 31 g. To 20 g of this salt was added 200 ml of methanol to give a suspension. Upon addition of dilute hydrochloric acid, the salt dissolved to liberate 10-mercaptodecyl methacrylate. This compound was extracted with n-hexane, the extract was dried with anhydrous magnesium sulfate, and n-hexane was evaporated away under reduced pressure. Thus, there was obtained 12 g of 10-mercaptodecyl methacrylate in the form of colorless transparent liquid.

This compound was analyzed by NMR (90 MHz, 10% CDCl$_3$ solution, at room temperature). The following NMR data was obtained.

$\delta = 5.35-5.00$ 5.90-6.05: ethylenic protons of methacryloyl group $\delta = 1.75-1.85$: methyl protons of methacryloyl group $\delta = 3.90-4.10$: protons of methylene adjacent to an oxygen atom $\delta = 2.15-2.60$: protons of methylene adjacent to a sulfur atom $\delta = 0.8-1.7$: remaining methyl protons and proton of mercapto group Mass spectroscopic analysis gave a molecular ion peak at m/e 258. Thus the compound was identified as 10-mercaptodecyl methacrylate.

(Production of disulfide compound)

Production Example 2

In 200 ml of ethanol was dissolved 10 g of 10-mercaptodecyl methacrylate. To the solution was added dropwise, with vigorous stirring, an ethanol solution of iodine until the color of iodine did not disappear any longer. Ethanol was evaporated away. To the residue was added 200 ml of methanol and the organic compound was extracted with hexane. Hexane was evaporated away. The major component of the residue was isolated by column chromatography (Wakogel C-200 (made by Wako Pure Chemical Industries, Ltd.) and hexane-ethyl acetate as an eluent). There was obtained 6.2 g of colorless transparent liquid.

This compound was analyzed by liquid chromatography. The chromatogram gave no peak of 10-mercaptodecyl methacrylate as the starting material, but gave a major peak (95.5%) at other elution time.

This compound was also analyzed by NMR (90 MHz, 10% CDCl$_3$ solution, at room temperature). The following NMR data was obtained.

$\delta = 5.00-5.35$ 5.90-6.05: ethylenic proton of methacryloyl group $\delta = 1.75-1.85$: methyl protons of methacryloyl group $\delta = 3.90-4.10$: protons of methylene adjacent to an oxygen atom $\delta = 2.15-2.60$: protons of methylene adjacent to a sulfur atom $\delta = 0.8-1.7$: remaining methylene protons Thus the compound was identified as bis(10-methacryloyloxydecyl)disulfide.

(Adhesive)

EXAMPLES 1 TO 13 AND COMPARATIVE EXAMPLES 1 AND 2

Thirteen compounds shown in Table 1 and the above-mentioned known compound N-(4-mercaptophenyl)-methacrylamide were examined for adhesion to precious metals in the following manner.

Each compound was dissolved in acetone to give a 1 wt % primer. The primer was applied by brushing to the following three adherends.

1) A pure gold plate, measuring 10×10×1 mm, polished with silicon carbide abrasive paper (1000 grit) and backed with a 4-mm thick stainless steel plate.

2) "Cast Well" of dental gold-silver-palladium alloy, measuring 10×10×1 mm, (made by G-C Dental Industrial Corp.) backed with a 4-mm thick stainless steel plate.

3) "Degudent Universal" of dental gold-platinum-palladium alloy, measuring 10×10×1 mm, (made by Mitsubishi Metal Corp.) backed with a 4-mm thick stainless steel plate.

One minute after application, the coating was washed with pure acetone so that only the molecules adsorbed on the surface remain. The washed coating was covered with a piece of adhesive tape having a hole 5 mm in diameter. The primer-coated surface exposed through the hole serves as an adherend.

On the other hand, a round rod of SUS304, measuring 7 mm in diameter and 25 mm long, was provided. The end of the rod was roughed by sand blasting with 50-μm alumina abrasive grains. On the roughed end was placed "Panavia EX" paste (a dental adhesive made by Kuraray Co., Ltd.) composed of 100 parts by weight of methacrylate ester, 3 parts by weight of sodium sulfinate-benzoyl peroxide-tertiary amine polymerization initiator, and 320 parts by weight of silane-treated inorganic filler. The rod end was pressed against the adherend to effect adhesion. One hour later, the bonded test pieces were immersed in water at 37° C. for 24 hours. After water immersion, the tensile bond strength was measured using a universal tester (made by Instron Ltd.) at a cross-head speed of 2 mm/min. An average of measurements of eight samples was obtained. The results are shown in Table 1.

TABLE 1

| Example No. | Primer compound | Adhesion to pure gold (kg/cm$^2$) | Adhesion to Cast Well (kg/cm$^2$) | Adhesion to Degudent Universal (kg/cm$^2$) |
|---|---|---|---|---|
| 1 | $H_2C=C(CH_3)-COSCH_2CH_2SH$ | 252 | 266 | 301 |
| 2 | $H_2C=C(CH_3)-COO{+CH_2}_5 SH$ | 292 | 318 | 343 |
| 3 | $H_2C=C(CH_3)-COO{+CH_2}_6 SH$ | 327 | 341 | 349 |
| 4 | $H_2C=C(CH_3)-COS{+CH_2}_6 SH$ | 301 | 325 | 337 |
| 5 | $H_2C=C(CH_3)-COO{+CH_2}_{10} SH$ | 348 | 356 | 374 |
| 6 | $H_2C=C(H)-COO{+CH_2}_{20} SH$ | 352 | 348 | 392 |
| 7 | $H_2C=C(H)-CONH{+CH_2}_{20} SH$ | 350 | 341 | 377 |
| 8 | $H_2C=C(CH_3)-COOCH_2CH_2O-C_6H_4-OCH_2CH_2SH$ | 353 | 347 | 381 |
| 9 | $H_2C=C(CH_3)-COO{+CH_2}_6 CHCH_2SH$ (with SH branch) | 365 | 359 | 388 |
| 10 | $H_2C=C(H)-S{+CH_2}_{10} SH$ | 315 | 333 | 339 |
| 11 | $H_2C=C(H)-OCO{+CH_2}_{11} SH$ | 305 | 296 | 314 |
| 12 | $H_2C=C(H)-SCO{+CH_2}_{11} SH$ | 326 | 343 | 324 |
| 13 | $H_2C=C(H)-C_6H_4-{+CH_2}_4 SH$ | 341 | 330 | 376 |
| Comparative Example 1 | N-(4-mercaptophenyl)-methacrylamide | 234 | 243 | 173 |

TABLE 1-continued

| Example No. | Primer compound | Adhesion to pure gold (kg/cm$^2$) | Adhesion to Cast Well (kg/cm$^2$) | Adhesion to Degudent Universal (kg/cm$^2$) |
|---|---|---|---|---|
| Comparative Example 2 | None | 171 | 151 | 128 |

EXAMPLES 14 TO 27

Fourteen compounds as shown in Table 2 were examined for adhesion to pure gold plate and "Degudent Universal" in the same manner as in Examples 1 to 13. The results are shown in Table 2.

TABLE 2

| Example No. | Primer compound | Adhesion to pure gold (kg/cm$^2$) | Adhesion to Degudent Universal (kg/cm$^2$) |
|---|---|---|---|
| 14 | $H_2C=\overset{H}{\underset{|}{C}}-COO(CH_2)_2SSCH_3$ | 243 | 274 |
| 15 | $H_2C=\overset{CH_3}{\underset{|}{C}}-COO(CH_2)_2SS(CH_2)_2OOC-\overset{CH_3}{\underset{|}{C}}=CH_2$ | 257 | 288 |
| 16 | $H_2C=\overset{CH_3}{\underset{|}{C}}-COSCH_2CH_2SSCH_2CH_2SOC-\overset{CH_3}{\underset{|}{C}}=CH_2$ | 248 | 276 |
| 17 | $H_2C=\overset{CH_3}{\underset{|}{C}}-COS(CH_2)_6SS(CH_2)_6SOC-\overset{CH_3}{\underset{|}{C}}=CH_2$ | 312 | 330 |
| 18 | $H_2C=\overset{CH_3}{\underset{|}{C}}-COO(CH_2)_6SS(CH_2)_6OOC-\overset{CH_3}{\underset{|}{C}}=CH_2$ | 325 | 338 |
| 19 | $H_2C=\overset{CH_3}{\underset{|}{C}}-COO(CH_2)_{10}SS(CH_2)_{10}OOC-\overset{CH_3}{\underset{|}{C}}=CH_2$ | 332 | 347 |
| 20 | $H_2C=\overset{H}{\underset{|}{C}}-S(CH_2)_{10}SS(CH_2)_{10}S-\overset{H}{\underset{|}{C}}=CH_2$ | 297 | 315 |
| 21 | $H_2C=\overset{H}{\underset{|}{C}}-OOC(CH_2)_{11}SS(CH_2)_{11}COO-\overset{H}{\underset{|}{C}}=CH_2$ | 271 | 293 |
| 22 | $H_2C=\overset{H}{\underset{|}{C}}-SOC(CH_2)_{11}SS(CH_2)_{11}COS-\overset{H}{\underset{|}{C}}=CH_2$ | 310 | 340 |
| 23 | $H_2C=\overset{H}{\underset{|}{C}}-COO(CH_2)_{20}SS(CH_2)_{20}OOC-\overset{H}{\underset{|}{C}}=CH_2$ | 335 | 343 |
| 24 | $H_2C=\overset{CH_3}{\underset{|}{C}}-CONH(CH_2)_{20}SS(CH_2)_{20}HNOC-\overset{CH_3}{\underset{|}{C}}=CH_2$ | 324 | 342 |
| 25 | $H_2C=\overset{H}{\underset{|}{C}}-\bigcirc-(CH_2)_4SS(CH_2)_4-\bigcirc-\overset{H}{\underset{|}{C}}=CH_2$ | 316 | 339 |
| 26 | $H_2C=\overset{CH_3}{\underset{|}{C}}-COO-CH_2CH_2O-\bigcirc-OCH_2CH_2-SS-CH_2CH_2O-\bigcirc-OCH_2CH_2-OOC\overset{CH_3}{\underset{|}{C}}=CH_2$ | 340 | 333 |

| Example No. | Primer compound | Adhesion to pure gold (kg/cm²) | Adhesion to Degudent Universal (kg/cm²) |
|---|---|---|---|
| 27 | H₂C=CH-⌬-CH₂-SS-CH₂-⌬-CH=CH₂ | 303 | 328 |

EXAMPLES 28 AND 29 AND COMPARATIVE EXAMPLE 3

The compound used in Example 5 was dissolved in acetone to give a 1% solution. The solution was applied to "Cast Well" according to the same procedure as in Examples 1 to 13. One minute after application, the coated surface was washed with pure acetone. A stainless steel rod was bonded with "Panavia EX" (made by Kuraray Co., Ltd.) (Example 28)

Test pieces were prepared in the same manner as above using the compound used in Example 19. (Example 29)

For comparison, test pieces were prepared in the same manner as above, except that the acetone solution was not applied to "Cast Well".

(Comparative Example 3)

One hour after bonding, the test pieces were immersed in water at 37° C. for 24 hours and then at 70° C. for 10 days. The tensile bond strength was measured in the same manner as in Example 1 to 13. The average bond strength was 280 kg/cm² and 165 kg/cm² in Examples 28 and 29, respectively, whereas it was 31 kg/cm² in Comparative Example 3.

EXAMPLES 30 AND 31 AND COMPARATIVE EXAMPLE 4

A two-part adhesive (paste type) of the following composition was prepared.

| Paste A | |
|---|---|
| Bis-GMA | 12.5 parts by weight |
| Triethyleneglycol dimethacrylate | 12.5 |
| Adhesive component in Example 5 | 0.1 |
| N,N-diethanol-p-toluidine | 0.5 |
| Silane-treated quartz powder | 74.5 |
| Paste B | |
| Bis-GMA | 12.5 parts by weight |
| Triethyleneglycol dimethacrylate | 12.5 |
| Benzoyl peroxide | 0.5 |
| Silane-treated quartz powder | 74.5 |

Paste A and paste B were mixed in equal amount to give an adhesive. Using this adhesive, a sand-blasted stainless steel rod was bonded to dental gold alloy ("Herador H", Au: 79%, Pt: 10%, Pd: 8%, made by Heraus Edulmetale GmbH in West Germany) polished with silicon carbide abrasive paper (1000 grit). Bonding was performed in the same manner as in Examples 1 to 13 except that the primer was not applied.

The test piece was immersed in water at 37° C. for 24 hours, and the tensile bond strength was measured. Failure took place at the interface between the gold alloy and the adhesive, and the average value (of 8 measurements) was 234 kg/cm². (Example 30)

The same procedure as mentioned above was repeated except that the adhesive component in Example 5 was replaced by the adhesive component in Example 19. The average strength was 201 kg/cm². (Example 31)

For comparison, the same procedure as Examples 30 and 31 was repeated except that paste A was replaced by paste A' (in which the adhesive component in Example 5 was excluded). Failure took place at the interface between the gold alloy and the adhesive, and the average value was 106 kg/cm². (Comparative Example 4)

EXAMPLE 32

A two-part adhesive (powder-liquid mix type) of the following composition was prepared.

| Powder component C | |
|---|---|
| Silane-treated silica powder | 100.0 parts by weight |
| Sodium benzenesulfinate | 0.4 |
| N,N-diethanol-p-toluidine | 0.5 |
| Liquid component D | |
| Bis-GMA | 50 parts by weight |
| 1,6-hexanediol dimethacrylate | 39 |
| 10-methacryloyloxydecyl dihydrogen phosphate | 10 |
| 10-mercaptodecyl methacrylate | 1 |
| Benzoyl peroxide | 1 |

A paste adhesive was prepared by mixing the powder component C (3 g) and the liquid component D (1 g). Using this paste adhesive, a sand-blasted stainless steel rod was bonded to dental gold alloy "Herador H" polished with silicon carbide abrasive paper (1000 grit). Bonding was performed in the same manner as in Examples 1 to 13 except that the primer was not applied.

The test piece was immersed in water at 37° C. for 24 hours, and the tensile bond strength was measured. Cohesive failure of the adhesive took place, and the average value (of 8 measurements) was 315 kg/cm².

What is claimed is:

1. In a method of adhering a metal to a second material, the improvement which comprises:
   adhering said metal to said second material with an adhesive composition containing a monomer having at least one mercapto group joined to a saturated carbon atom and at least one olefinic double bond and which has the formula:

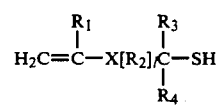

wherein $R_1$ is hydrogen or methyl; $R_2$ is a $C_1$–$C_{40}$ organic group, a $C_1$–$C_{40}$ organic group containing a

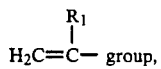

a $C_1$–$C_{40}$ organic group containing a mercapto group or a $C_1$–$C_{40}$ organic group containing both a mercapto group and a

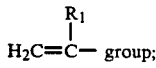

$R_3$ and $R_4$ each represent a $C_1$–$C_{40}$ organic group, a $C_1$–$C_{40}$ organic group substituted by a

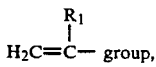

a $C_1$–$C_{40}$ organic group substituted by a mercapto group or a $C_1$–$C_{40}$ organic group substituted by both a mercapto group and a

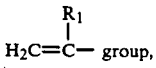

hydrogen, mercapto or halogen; at least two of $R_2$, $R_3$ and $R_4$ may join together to form a cyclic structure when at least one of $R_3$ and $R_4$ is an organic group; X is

—COO—, —OOC—, —CONH—, —COS—, —SOC—,

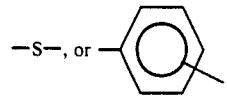

and l is 0 or 1.

2. The method of claim 1, wherein the compound has the formula:

wherein $R_1$ is hydrogen or methyl, and m denotes an integer of 6 to 20.

3. The method of claim 1, wherein the composition comprises said monomer and an inert volatile organic solvent.

4. The method of claim 1, wherein the composition comprises said monomer and at least one copolymerizable monomer with said compound.

5. The method of claim 4, wherein the composition comprises said monomer, at least one copolymerizable monomer with said compound and a polymerization initiator.

6. The method of claim 1, which comprises applying said composition to the surface of said metal, applying a second adhesive composition comprising a copolymerizable olefinic monomer with said compound and a polymerization initiator to the thin layer of said composition on said metal and then adhering said second material to said film covered metal.

7. The method of claim 1, which comprises applying said composition to the surface of said metal, applying a second composition comprising a copolymerizable olefinic monomer with said monomer and a polymerization initiator to the surface of said second material and then adhering said metal to said second material by bringing the coated surfaces of both materials into contact with each other.

8. The method of claim 1, wherein said metal is dental metal and said second material is a tooth or a restorative dental material.

* * * * *